(12) United States Patent
Moore

(10) Patent No.: US 11,730,590 B2
(45) Date of Patent: Aug. 22, 2023

(54) LOW PROFILE EXPANDABLE HEART VALVE

(71) Applicant: St. Jude Medical, Cardiology Division, Inc., St. Paul, MN (US)

(72) Inventor: Brandon Moore, St. Louis Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 190 days.

(21) Appl. No.: 17/381,358

(22) Filed: Jul. 21, 2021

(65) Prior Publication Data

US 2022/0023037 A1  Jan. 27, 2022

Related U.S. Application Data

(60) Provisional application No. 63/055,402, filed on Jul. 23, 2020.

(51) Int. Cl.
| | | |
|---|---|---|
| *A61F 2/24* | (2006.01) | |
| *A61F 2/82* | (2013.01) | |
| *A61B 17/04* | (2006.01) | |

(52) U.S. Cl.
CPC ......... *A61F 2/2418* (2013.01); *A61F 2/2433* (2013.01); *A61F 2220/0075* (2013.01); *A61F 2230/0017* (2013.01); *A61F 2230/0054* (2013.01)

(58) Field of Classification Search
None
See application file for complete search history.

(56) References Cited

U.S. PATENT DOCUMENTS

| | | | |
|---|---|---|---|
| 6,488,702 B1 * | 12/2002 | Besselink | A61F 2/915 606/155 |
| 7,818,861 B2 | 10/2010 | Sokel | |
| 8,454,685 B2 * | 6/2013 | Hariton | E03C 1/066 623/2.17 |
| 9,326,856 B2 | 5/2016 | Schraut et al. | |
| 10,166,097 B2 * | 1/2019 | Quadri | A61F 2/2427 |
| 10,179,047 B2 | 1/2019 | Lee et al. | |
| 10,413,284 B2 * | 9/2019 | McNamara | A61B 17/221 |
| 11,039,921 B2 * | 6/2021 | Tegels | A61F 2/2418 |
| 11,179,254 B2 * | 11/2021 | White | A61F 2/243 |
| 11,197,754 B2 * | 12/2021 | Saffari | A61F 2/2418 |

(Continued)

FOREIGN PATENT DOCUMENTS

WO   2022020415 A1   1/2022

OTHER PUBLICATIONS

International Search Report for Application No. PCT/US2021/042472 dated Nov. 9, 2021, 2 Pages.

*Primary Examiner* — Ann Schillinger
(74) *Attorney, Agent, or Firm* — Sleman & Lund LLP

(57) ABSTRACT

A prosthetic heart valve includes a radially collapsible and expandable stent, a cuff and leaflets sutured thereto. The heart valve extends axially between an inflow end and an outflow end and the stent includes a layout of struts and nodes having a hybrid combination of vertical struts and oblique struts in the form of diamond-shaped and half diamond-shaped cells. The layout of the structure is configured to preserve a low cell density of material used in the stent to reduce the stent profile while in a collapsed state and to improve the deployment accuracy of the stent into the native valve annulus.

12 Claims, 11 Drawing Sheets

(56) References Cited

U.S. PATENT DOCUMENTS

| | | | |
|---|---|---|---|
| 2005/0234546 A1* | 10/2005 | Nugent | A61F 2/2433 623/2.11 |
| 2006/0095115 A1* | 5/2006 | Bladillah | A61F 2/2418 623/1.24 |
| 2008/0004688 A1 | 1/2008 | Spenser et al. | |
| 2011/0146361 A1* | 6/2011 | Davidson | A61F 2/2418 72/53 |
| 2012/0035712 A1* | 2/2012 | Maisano | A61F 2/915 623/2.11 |
| 2014/0155990 A1* | 6/2014 | Nyuli | A61F 2/2436 623/2.11 |
| 2014/0236287 A1* | 8/2014 | Clague | A61F 2/2418 623/2.11 |
| 2014/0330368 A1* | 11/2014 | Gloss | A61F 2/243 623/2.11 |
| 2015/0094802 A1* | 4/2015 | Buchbinder | A61F 2/2454 623/2.38 |
| 2015/0209141 A1* | 7/2015 | Braido | A61F 2/2418 623/2.17 |
| 2015/0282931 A1* | 10/2015 | Brunnett | A61F 2/2466 623/2.37 |
| 2016/0038280 A1* | 2/2016 | Morriss | A61F 2/2436 623/2.18 |
| 2018/0055634 A1* | 3/2018 | White | A61F 2/2427 |
| 2018/0318077 A1* | 11/2018 | Ness | A61F 2/2427 |
| 2018/0353291 A1* | 12/2018 | Benson | A61F 2/2418 |
| 2019/0151084 A1* | 5/2019 | Pintor | A61F 2/2418 |
| 2022/0338978 A1* | 10/2022 | Yushtein | A61F 2/2418 |
| 2023/0024690 A1* | 1/2023 | Cohen | A61F 2/243 |
| 2023/0052124 A1* | 2/2023 | Cohen | A61F 2/243 |

\* cited by examiner

LOW PROFILE EXPANDABLE HEART VALVE

CROSS-REFERENCE TO RELATED APPLICATIONS

This application claims the benefit of the filing date of U.S. Provisional Patent Application No. 63/055,402 filed Jul. 23, 2020, the disclosure of which is hereby incorporated by reference herein.

BACKGROUND OF THE DISCLOSURE

Valvular heart disease, and specifically aortic and mitral valve disease, is a significant health issue in the United States. Valve replacement is one option for treating heart valve diseases. Prosthetic heart valves, including surgical heart valves and collapsible/expandable heart valves intended for transcatheter aortic valve replacement ("TAVR") or transcatheter mitral valve replacement ("TMVR"), are well known in the patent literature. Surgical or mechanical heart valves may be sutured into a native annulus of a patient during an open-heart surgical procedure, for example. Collapsible/expandable heart valves may be delivered into a patient via a tube-like delivery apparatus such as a catheter, a trocar, a laparoscopic instrument, or the like to avoid a more invasive procedure such as full open-chest, open-heart surgery. As used herein, reference to a "collapsible/expandable" heart valve includes heart valves that are formed with a small cross-section that enables them to be delivered into a patient through a tube-like delivery apparatus in a minimally invasive procedure, and then expanded to an operable state once in place, as well as heart valves that, after construction, are first collapsed to a small cross-section for delivery into a patient and then expanded to an operable size once in place in the valve annulus.

Collapsible/expandable prosthetic heart valves typically take the form of a one-way valve structure (often referred to herein as a valve assembly) mounted to/within an expandable stent. In general, these collapsible/expandable heart valves include a self-expanding or balloon-expandable stent, often made of nitinol or another shape-memory metal or metal alloy (for self-expanding stents) or steel or cobalt chromium (for balloon-expandable stents). Existing collapsible/expandable TAVR devices have been known to use one of two stent layouts—straight vertical struts connected by "V"s as illustrated in U.S. Pat. No. 8,454,685, or diamond-shaped cell layouts as illustrated in U.S. Pat. No. 9,326,856, both of which are herein incorporated by reference. The one-way valve assembly mounted to/within the stent includes one or more leaflets, and may also include a cuff or skirt. The cuff may be disposed on the stent's interior or luminal surface, its exterior or abluminal surface, and/or on both surfaces. A cuff helps to ensure that blood does not just flow around the valve leaflets if the valve or valve assembly are not optimally seated in a valve annulus. A cuff, or a portion of a cuff disposed on the exterior of the stent, can help retard leakage around the outside of the valve (the latter known as paravalvular leakage or "PV" leakage).

One challenge facing TAVR devices is delivery system profile. Delivery system profile is characterized by radial size, particularly when in the collapsed condition, with smaller sizes being desirable for safely navigating through small vessels. In other words, if a prosthetic heart valve can be collapsed to a smaller size, a delivery device used to deliver the prosthetic heart valve can have a correspondingly smaller size, which is generally desirable to allow for easier and safer passage of the delivery device through the vasculature. Stents that do not foreshorten, such as stents that include vertical bars extending along most or the entire length of the stent, may result in relatively large profiles when the stent is collapsed, since the bulk of the stent cannot be spread over a longer distance when the stent is collapsed. Another challenge facing TAVR devices is deployment accuracy of the prosthetic valve in the native valve annulus. Deployment accuracy refers to the ability to deploy the valve at the target implantation depth. In other words, the positioning of the prosthetic valve with respect to native anatomical structures, such as the native valve annulus and the native leaflets, may affect the performance of the prosthetic heart valve. Poor deployment accuracy can result in a less-than-optimal placement of the prosthetic heart valve relative to the native anatomical structures, potentially resulting in negative patient outcomes such as regurgitation or conduction disturbances leading to the need for a permanent pacemaker.

In connection with deployment accuracy, a prosthetic valve that is delivered to a native valve annulus in a collapsed state may undergo foreshortening upon expansion of the stent. During foreshortening, the inflow and outflow ends of the stent draw closer together toward each other, which may frustrate the desired alignment of the valve within the native annulus. For example, stents that are formed mostly or entirely of diamond-shaped cells will foreshorten during expansion when the valve is deployed at the native valve annulus. If a surgeon aligns the prosthetic heart valve in a desired position relative to the valve annulus while the prosthetic heart valve is collapsed within a delivery device, as the prosthetic heart valve is deployed from the delivery device and begins to expand, the ends of the prosthetic heart valve will move closer together as the stent foreshortens, which may result in the original alignment changing or being lost.

Accordingly, methods and devices for decreasing the profile of the prosthetic heart valve and improving deployment accuracy are desirable.

BRIEF SUMMARY OF THE DISCLOSURE

This disclosure describes a prosthetic aortic valve having features that may help address the challenges described above. For example, to help maintain a low profile of the prosthetic heart valve in the delivery device, the disclosed device may include a low cell density (or low volume of stent material compared to prosthetic heart valves that are otherwise similarly sized), thus reducing the volume and profile of the device. The disclosed device may also have some amount of lengthening and foreshortening when collapsing and expanding, which may help "spread" the volume of the device over a longer distance when the stent is in the collapsed condition. As noted above, smaller sizes are desirable for safely navigating through small vessels. Further, the structure of the stent provides strategic foreshortening that improves the accuracy with which the valve is deployed, as will be discussed below in further detail. The stent is formed of a material capable of being crimped to and sustaining a collapsed state which axially lengthens the stent and decreases the profile while collapsed. Such materials may include cobalt chromium or stainless steel. The stent is crimped over an expandable balloon in preparation for delivery to the native valve annulus. The balloon is configured to expand at the direction of a user upon delivery to the native annulus causing expansion of the stent in the radial direction and foreshortening in the axial direction. The foreshortening is directional, meaning nodes near the outflow end of the stent move down toward the annulus upon expansion, while nodes at the inflow end of the stent do not move axially at all (or only minimally) Keeping inflow nodes at the same depth relative to the anatomy throughout balloon expansion may help maximize deployment accuracy and may help limit the risks associated with sub-optimal positioning of the prosthetic heart valve.

According to a first aspect of the disclosure, a prosthetic heart valve includes a stent, a cuff and a plurality of prosthetic leaflets. The stent may be collapsible and expandable, extending in an axial direction from a first inflow end to a second outflow end. The stent may have a plurality of vertical struts that are parallel to the axial direction in an expanded condition of the stent. The stent may also have a plurality of oblique struts that are oblique to the axial direction in the expanded condition of the stent. The cuff may be coupled to the stent. The prosthetic leaflets may be disposed within the stent. The leaflets may be configured to allow blood to flow in an antegrade direction from the first inflow end toward the second outflow end of the stent. The leaflets may substantially block blood from flowing in a retrograde direction from the second outflow end of the stent toward the first inflow end of the stent. The plurality of oblique struts may be coupled to the plurality of vertical struts so that, upon transitioning from the collapsed condition to the expanded condition, the first inflow end of the stent may remain substantially static relative to the axial direction while the second outflow end of the stent may move in the axial direction toward the first inflow end.

According to another embodiment of the disclosure, a method of implanting a prosthetic heart valve into a native valve annulus includes positioning the prosthetic heart valve in a collapsed condition over an expandable balloon attached to a delivery system such that the prosthetic heart valve surrounds the expandable balloon. The prosthetic heart valve may have a first inflow end disposed at a first axial position on the expandable balloon and a second outflow end disposed at a second axial position on the expandable balloon. The delivery system may be inserted through a patient until the prosthetic heart valve is adjacent the native valve annulus. The first inflow end of the prosthetic heart valve may be aligned with a desired axial location in the native valve annulus while the prosthetic heart valve is in the collapsed condition. The balloon may be expanded to transition the prosthetic heart valve into an expanded condition such that the prosthetic heart valve radially expands and axially foreshortens. During radial expansion, the first inflow end of the prosthetic heart valve may axially translate no more than 4 millimeters from the first axial position.

DETAILED DESCRIPTION

As used herein, the term "inflow end" when used in connection with a prosthetic heart valve refers to the end of the prosthetic valve into which blood first enters when the prosthetic valve is implanted in an intended position and orientation, while the term "outflow end" refers to the end of the prosthetic valve where blood exits when the prosthetic valve is implanted in the intended position and orientation. Thus, for a prosthetic aortic valve, the inflow end is the end nearer the left ventricle while the outflow end is the end nearer the aorta. The intended position and orientation are used for the convenience of describing the valve disclosed herein, however, it should be noted that the use of the valve is not limited to the intended position and orientation, but may be deployed in any type of lumen or passageway. For example, although the prosthetic heart valve is described herein as a prosthetic aortic valve, the same or similar structures and features can be employed in other heart valves, such as the pulmonary valve, the mitral valve, or the tricuspid valve. As used herein, the terms "substantially," "generally," "approximately," and "about" are intended to mean that slight deviations from absolute are included within the scope of the term so modified. As used herein, the stent may assume an "expanded state" and a "collapsed state," which refer to the relative radial size of the stent.

Figure 1:
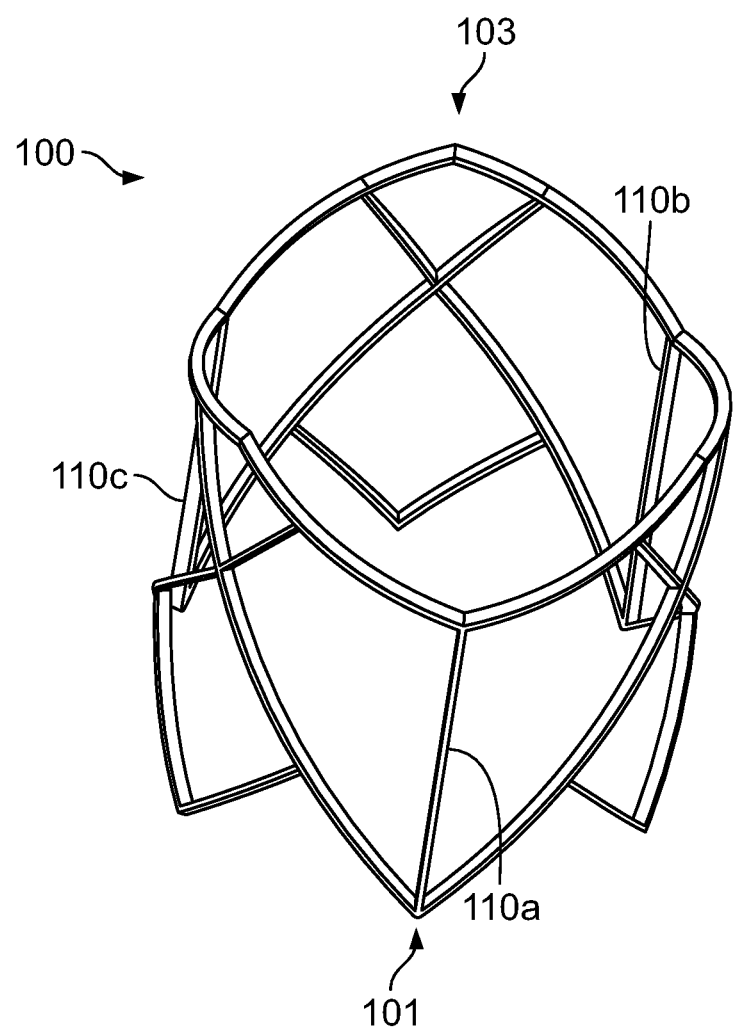
FIG. 1 is a perspective view of a stent of a prosthetic heart valve according to an embodiment of the disclosure.

FIG. 1 illustrates a perspective view of a stent 100 of a prosthetic heart valve according to an embodiment of the disclosure. Stent 100 may include a frame extending in an axial direction between an inflow end 101 and an outflow end 103. Stent 100 includes three generally symmetric sections, wherein each section spans about 120 degrees around the circumference of stent 100. Stent 100 includes three vertical struts 110a, 110b, 110c, that extend in an axial direction substantially parallel to the direction of blood flow through the stent, which may also be referred to as a central longitudinal axis. Each vertical strut 110a, 110b, 110c may extend substantially the entire axial length between the inflow end 101 and the outflow end 103 of the stent 100, and may be disposed between and shared by two sections. In other words, each section is defined by the portion of stent 100 between two vertical struts. Thus, each vertical strut 110a, 110b, 110c is also separated by about 120 degrees around the circumference of stent 100. It should be understood that, if stent 100 is used in a prosthetic heart valve having three leaflets, the stent may include three sections as illustrated. However, in other embodiments, if the prosthetic heart valve has two leaflets, the stent may only include two of the sections.

Figure 2:
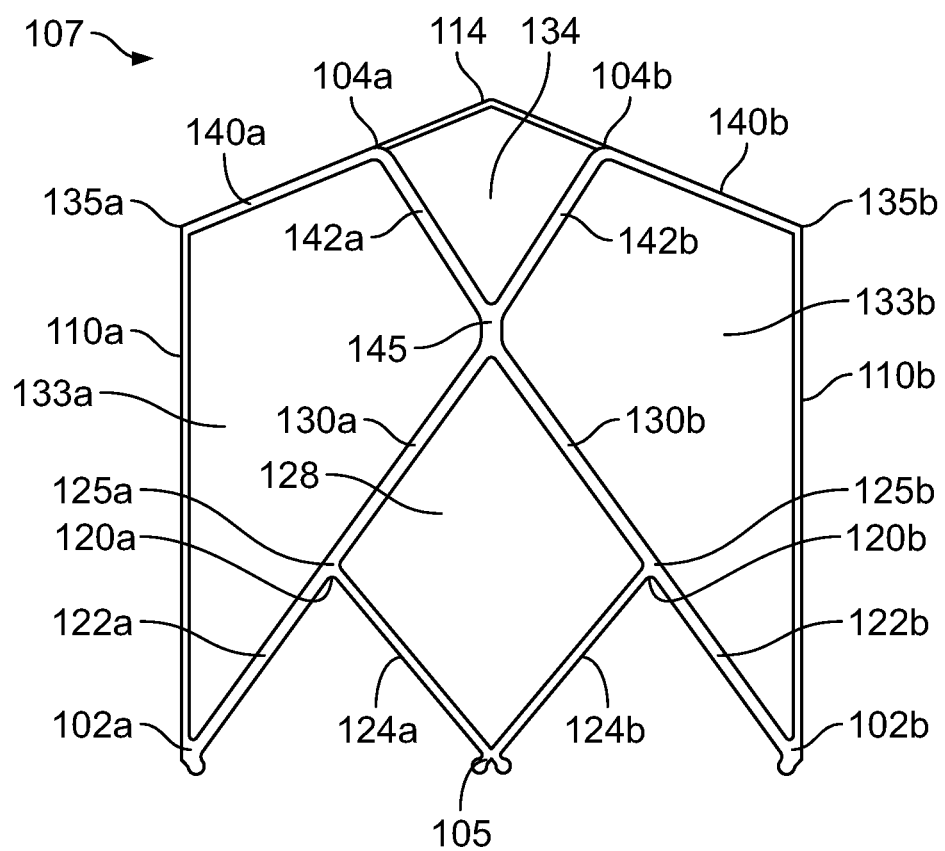
FIG. 2 is a schematic front view of a section of the stent of FIG. 1.

FIG. 2 illustrates a schematic view of a stent section 107 of stent 100, which will be described herein in greater detail and which is representative of all three sections. Stent section 107 depicted in FIG. 2 includes a first vertical strut 110a and a second vertical strut 110b. First vertical strut 110a extends axially between a first inflow node 102a and a first outer node 135a. Second vertical strut 110b extends axially between a second inflow node 102b and a second outer node 135b. As is illustrated, the vertical struts 110a, 110b may extend almost the entire axial length of stent 100. In some embodiments, stent 100 may be formed as an integral unit, for example by laser cutting the stent from a tube. The term "node" may refer to where two or more struts of the stent 100 meet one another. A pair of sequential inverted V's extends between inflow nodes 102a, 102b, which includes a first inflow inverted V 120a and a second inflow inverted V 120b coupled to each other at an inflow node 105. First inflow inverted V 120a comprises a first outer lower strut 122a extending between first inflow node 102a and a first central node 125a. First inflow inverted V 120a further comprises a first inner lower strut 124a extending between first central node 125a and inflow node 105. A second inflow inverted V 120b comprises a second inner lower strut 124b extending between inflow node 105 and a second central node 125b. Second inflow inverted V 120b further comprises a second outer lower strut 122b extending between second central node 125b and second inflow node 102b. Although described as inverted V's, these structures may also be described as half-cells, each half cell being a half-diamond cell with the open portion of the half-cell at the inflow end 101 of the stent 100.

Stent section 107 further includes a first central strut 130a extending between first central node 125a and an upper node 145. Stent section 107 also includes a second central strut 130b extending between second central node 125b and upper node 145. First central strut 130a, second central strut 130b, first inner lower strut 124a and second inner lower strut 124b form a diamond cell 128. Stent section 107 includes a first outer upper strut 140a extending between first outer node 135 and a first outflow node 104a. Stent section 107 further includes a second outer upper strut 140b extending between second outer node 135b and a second outflow node 104b. Stent section 107 includes a first inner upper strut 142a extending between first outflow node 104a and upper node 145. Stent section 107 further includes a second inner upper strut 142b extending between upper node 145 and second outflow node 104b. Stent section 107 includes an outflow inverted V 114 which extends between first and second outflow nodes 104a, 104b. First vertical strut 110a, first outer upper strut 140a, first inner upper strut 142a, first central strut 130a and first outer lower strut 122a form a first generally kite-shaped cell 133a. Second vertical strut 110b, second outer upper strut 140b, second inner upper strut 142b, second central strut 130b and second outer lower strut 122b form a second generally kite-shaped cell 133b. First and second kite-shaped cells 133a, 133b are symmetric and opposite each other on stent section 107. Although the term "kite-shaped," is used above, it should be understood that such a shape is not limited to the exact geometric definition of kite-shaped. Outflow inverted V 114, first inner upper strut 142a and second inner upper strut 142b form upper cell 134. Upper cell 134 is generally kite-shaped and axially aligned with diamond cell 128 on stent section 107. It should be understood that, although designated as separate struts, the various struts described herein may be part of a single unitary structure as noted above. However, in other embodiments, stent 100 need not be formed as an integral structure and thus the struts may be different structures (or parts of different structures) that are coupled together.

Figure 3:
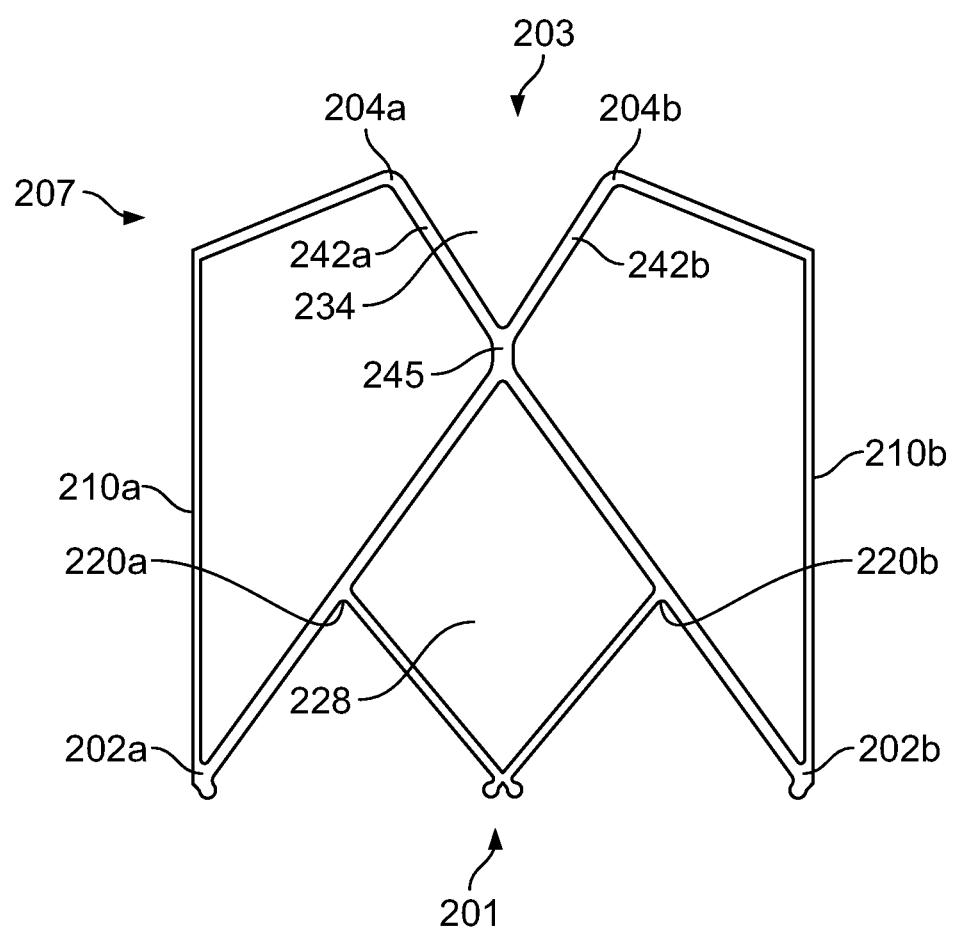
FIG. 3 is a schematic front view of a section of a stent according to an alternate embodiment of a prosthetic heart valve.

FIG. 3 illustrates a schematic view of a stent section 207 according to an alternate embodiment of the disclosure. Unless otherwise stated, like reference numerals refer to like elements of above-described stent 100 but within the 200-series of numbers. Stent section 207 is substantially similar to stent section 107, including inflow nodes 202a, 202b, vertical struts 210a, 210b, first and second inflow inverted V's 220a, 220b and outflow nodes 204a, 204b. The structure of stent section 207 departs from that of stent section 107 in that it does not include an outflow inverted V. The purpose of an embodiment having such structure of stent section 207 shown in FIG. 3 is to reduce the required force to expand the outflow end 203 of the stent 200, compared to stent 100, to promote uniform expansion relative to the inflow end 201. Outflow nodes 204a, 204b are connected by a properly oriented V formed by first inner upper strut 242a, upper node 245 and second inner upper strut 242b. In other words, struts 242a, 242b may form a half diamond cell 234, with the open end of the half-cell oriented toward the outflow end 203. Half diamond cell 234 is axially aligned with diamond cell 228. Adding an outflow inverted V coupled between outflow nodes 204a, 204b contributes additional material that increases resistance to modifying the stent shape and requires additional force to expand the stent. The exclusion of material from outflow end 203 decreases resistance to expansion on outflow end 203, which may promote uniform expansion of inflow end 201 and outflow end 203. In other words, the inflow end 201 of stent 200 does not include continuous circumferential structure, but rather has mostly or entirely open half-cells with the open portion of the half-cells oriented toward the inflow end 201, whereas most of the outflow end 203 includes substantially continuous circumferential structure, via struts that correspond with struts 140a, 140b. All else being equal, a substantially continuous circumferential structure may require more force to expand compared to a similar but open structure. Thus, the inflow end 101 of stent 100 may require more force to radially expand compared to the outflow end 103. By omitting inverted V 114, resulting in stent 200, the force required to expand the outflow end 203 of stent 200 may be reduced to an amount closer to the inflow end 201.

Figure 4A:
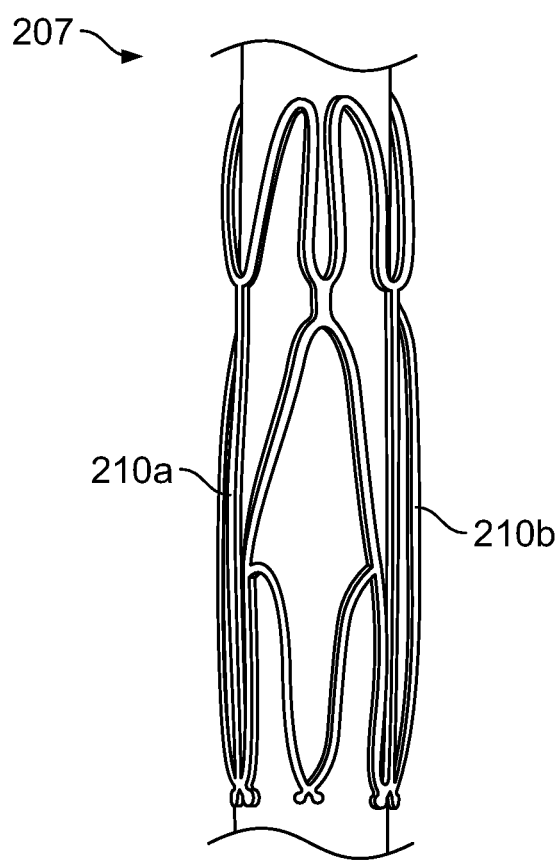
FIGS. 4A-B are front views of the stent section of FIG. 3 in a collapsed and expanded state, respectively.
Figure 4B:
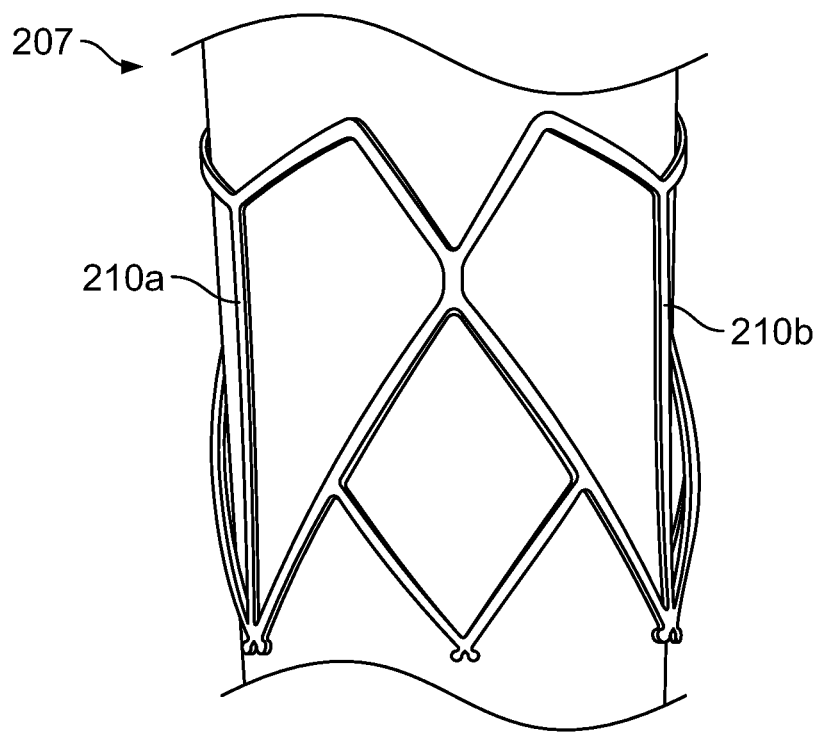
Figure 5A:
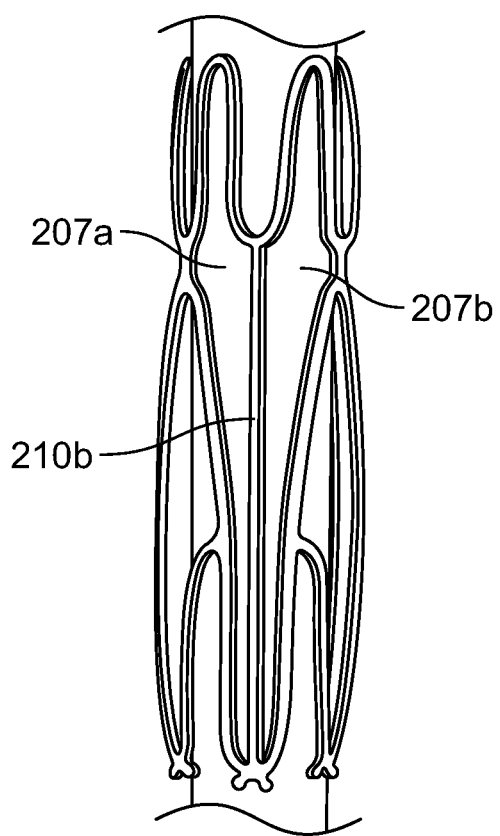
FIGS. 5A-B are side views of a portion of the stent according to the embodiment of FIG. 3 in a collapsed and expanded state, respectively.
Figure 5B:
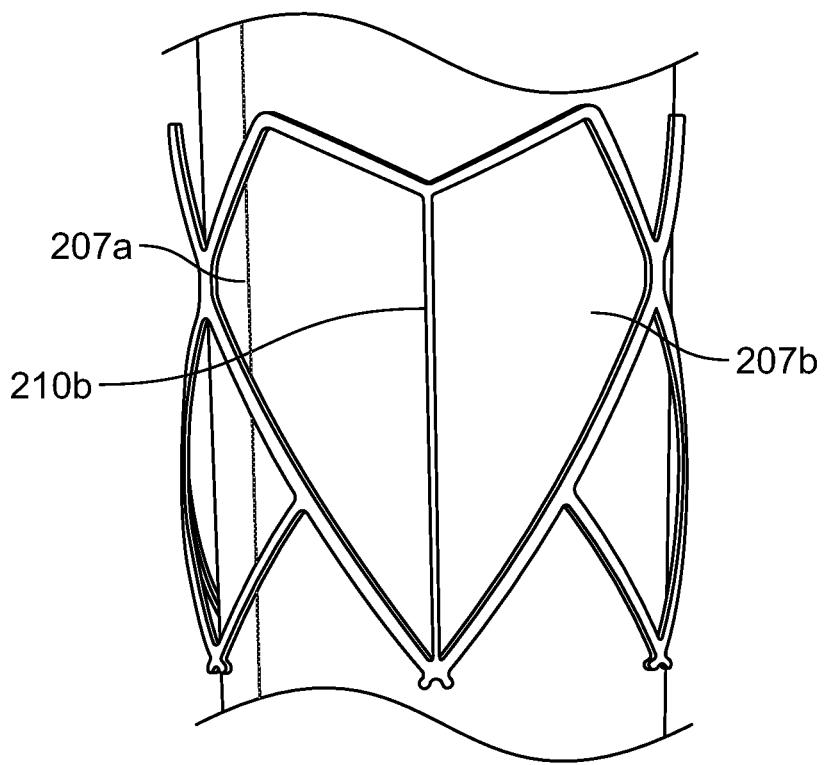

FIG. 4A shows a front view of stent section 207 in a collapsed state and FIG. 4B shows a front view of stent section 207 in an expanded state. It should be understood that stent 200 in FIGS. 4A-B is illustrated with an opaque tube extending through the interior of the stent, purely for the purpose of helping illustrate the stent. As described above, a stent comprises three symmetric sections, each section spanning about 120 degrees around the circumference of the stent. Stent section 207 illustrated in FIGS. 4A-B is defined by the region between vertical struts 210a, 210b. Stent section 207 is representative of all three sections of the stent. Stent section 207 has an arcuate structure such that when three sections are connected, they form one complete cylindrical shape. FIGS. 5A-B illustrate a portion of the stent from a side view. In other words, the view of stent 200 in FIGS. 5A-B is rotated about 60 degrees compared to the view of FIGS. 4A-B. The view of the stent depicted in FIGS. 5A-B is centered on vertical strut 210b showing approximately half of each of two adjacent stent sections 207a, 207b on each side of vertical strut 210b. Sections 207a, 207b surrounding vertical strut 210b are mirror images of each other. FIG. 5A shows stent sections 207a, 207b in a collapsed state whereas FIG. 5B shows stent sections 207a, 207b in an expanded state.

Figure 6:
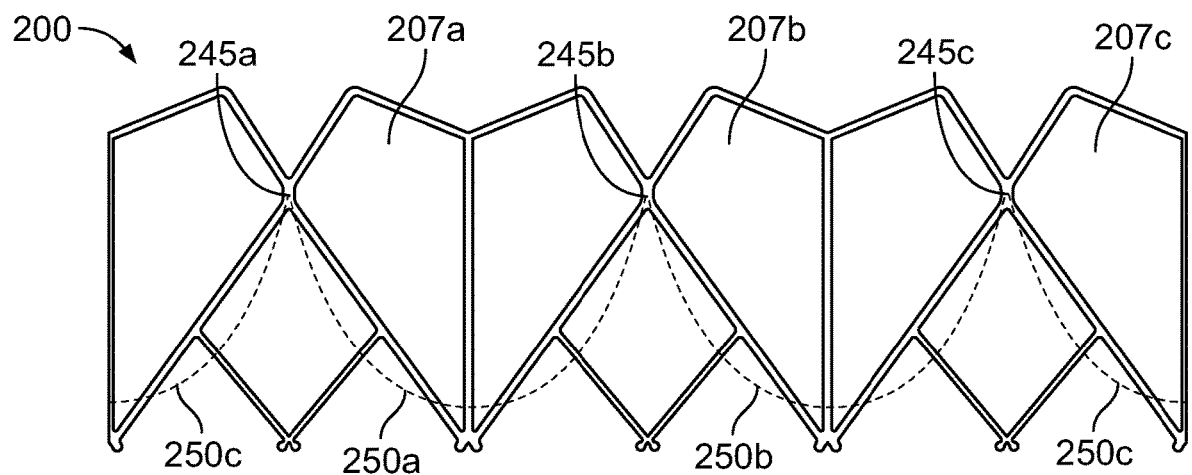
FIG. 6 is a flattened view of the stent according to the embodiment of FIG. 3, as if cut and rolled flat.

FIG. 6 illustrates a flattened view of stent 200 including three stent sections 207a, 207b, 207c, as if the stent has been cut longitudinally and laid flat on a table. As depicted, sections 207a, 207b, 207c are symmetric to each other and adjacent sections share a common vertical strut. As described above, stent 200 is shown in a flattened view, but each section 207a, 207b, 207c has an arcuate shape spanning 120 degrees to form a full cylinder. Further depicted in FIG. 6 are leaflets 250a, 250b, 250c coupled to stent 200. However, it should be understood that only the connection of leaflets 250a-c is illustrated in FIG. 6. In other words, each leaflet 250a-c would typically include a free edge, with the free edges acting to coapt with one another to prevent retrograde flow of blood through the stent 200, and the free edges moving radially outward toward the interior surface of the stent to allow antegrade flow of blood through the stent. Those free edges are not illustrated in FIG. 6. Rather, the attached edges of the leaflets 250a-c are illustrated in dashed lines in FIG. 6. Although the attachment may be via any suitable modality, the attached edges may be preferably sutured to the stent 200 and/or to an intervening cuff or skirt between the stent and the leaflets 250a-c. Each of the three leaflets 250a, 250b, 250c, extends about 120 degrees around stent 200 from end to end and each leaflet includes a belly that may extend toward the radial center of stent 200 when the leaflets are coapted together. Each leaflet extends between the upper nodes of adjacent sections. First leaflet 250a extends from first upper node 245a of first stent section 207a to second upper node 245b of second stent section 207b. Second leaflet 250b extends from second upper node 245b to third upper node 245c of third stent section 207c. Third leaflet 250c extends from third upper node 245c to first upper node 245a. As such, each upper node includes a first end of a first leaflet and a second end of a second leaflet coupled thereto. In the illustrated embodiment, each end of each leaflet is coupled to its respective node by suture. However, any coupling means may be used to attach the leaflets to the stent. It is further contemplated that the stent may include any number of sections and/or leaflets. For example, the stent may include two sections, wherein each section extends 180 degrees around the circumference of the stent. Further, the stent may include two leaflets to mimic a bicuspid valve. Further, it should be noted that each leaflet may include tabs or other structures (not illustrated) at the junction between the free edges and attached edges of the leaflets, and each tab of each leaflet may be coupled to a tab of an adjacent leaflet to form commissures. In the illustrated embodiment, the leaflet commissures are illustrated attached to nodes where struts intersect. However, in other embodiments, the stent 200 may include commissure attachment features built into the stent to facilitate such attachment. For example, commissures attachment features may be formed into the stent 200 at nodes 245a-c, with the commissure attachment features including one or more apertures to facilitate suturing the leaflet commissures to the stent. Further, leaflets 250a-c may be formed of a biological material, such as animal pericardium, or may otherwise be formed of synthetic materials, such as ultra-high molecular weight polyethylene (UHMWPE).

Figure 7A:
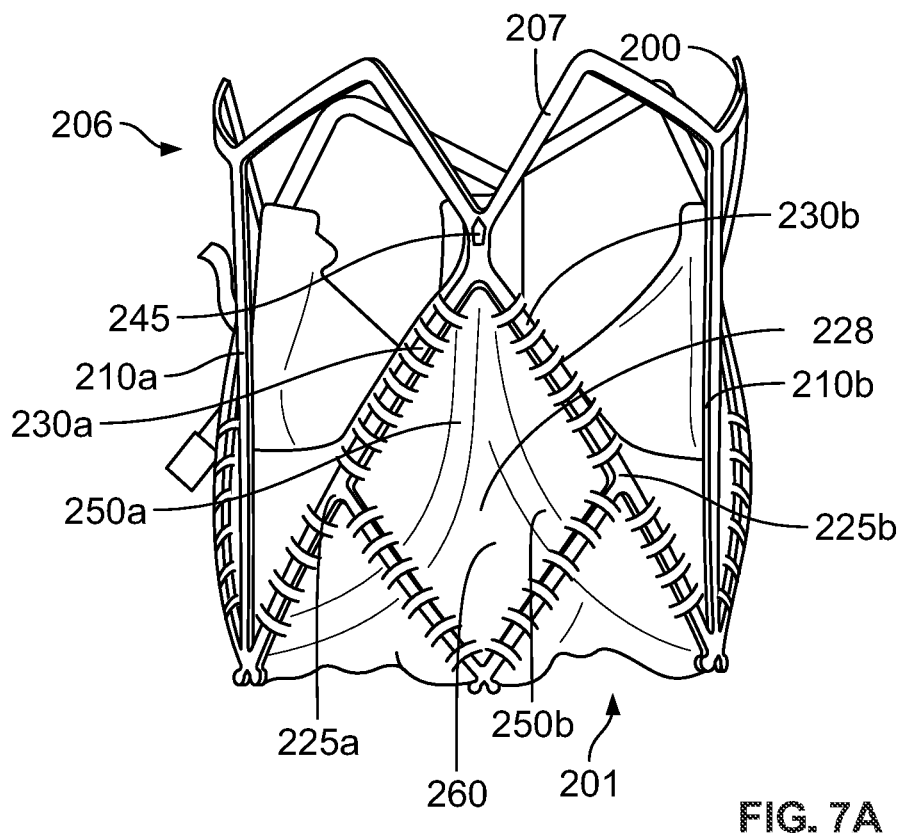
FIGS. 7A-B are front and side views, respectively, of a prosthetic heart valve including the stent of FIG. 6.
Figure 7B:
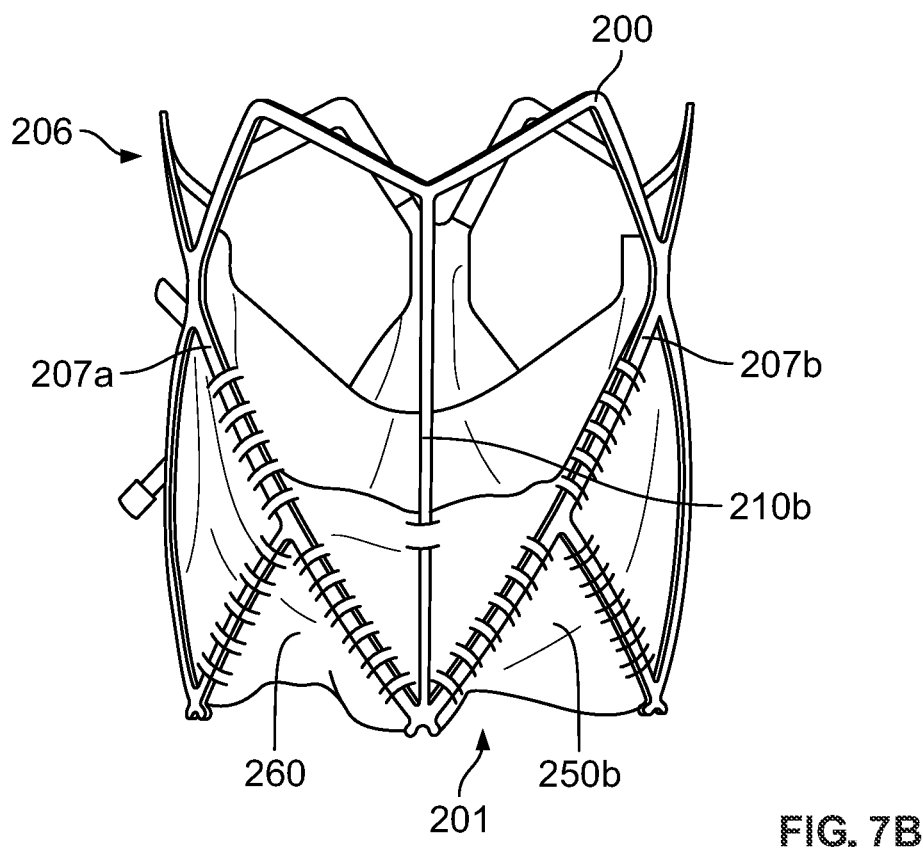

FIGS. 7A-B illustrate prosthetic heart valve 206, which includes stent 200, a cuff 260 coupled to stent 200 (for example via sutures) and leaflets 250a, 250b, 250c attached to stent 200 and/or cuff 260 (for example via sutures). Prosthetic heart valve 206 is intended for use in replacing an aortic valve, although the same or similar structures may be used in a prosthetic valve for replacing other heart valves. Cuff 260 is disposed on a luminal or interior surface of stent 200, although the cuff could be disposed alternately or additionally on an abluminal or exterior surface of the stent.

The cuff 250 may include an inflow end disposed substantially along inflow end 201 of stent 200. FIG. 7A shows a front view of valve 206 showing one stent portion 207 between vertical struts 210a, 210b including cuff 260 and an outline of two leaflets 250a, 250b sutured to cuff 260. Different methods of suturing leaflets to the cuff as well as the leaflets and/or cuff to the stent may be used, many of which are described in U.S. Pat. No. 9,326,856 which is herein incorporated by reference. In the illustrated embodiment, the upper (or outflow) edge of cuff 260 is sutured to first central node 225a, upper node 245 and second central node 225b, extending along first central strut 230a and second central strut 230b. The upper (or outflow) edge of cuff 260 continues extending approximately between the second central node of one section and the first central node of an adjacent section. Cuff 260 extends between upper node 245 and inflow end 201. Thus, cuff 260 covers the cells of stent portion 207 formed by the struts between upper node 245 and inflow end 201, including diamond cell 228. FIG. 7B illustrates a side view of stent 200 including cuff 260 and an outline of leaflet 250b. In other words, the view of valve 206 in FIG. 7B is rotated about 60 degrees compared to the view of FIG. 7A. The view depicted in FIG. 7B is centered on vertical strut 210b showing approximately half of each of two adjacent stent sections 207a, 207b on each side of vertical strut 210b. Sections 207a, 207b surrounding vertical strut 210b are mirror images of each other. As described above, the cuff may be disposed on the stent's interior or luminal surface, its exterior or abluminal surface, and/or on both surfaces. A cuff ensures that blood does not just flow around the valve leaflets if the valve or valve assembly are not optimally seated in a valve annulus. A cuff, or a portion of a cuff disposed on the exterior of the stent, can help retard leakage around the outside of the valve (the latter known as paravalvular leakage or "PV" leakage). In the embodiment illustrated in FIGS. 7A-B, the cuff 260 only covers about half of the stent 200, leaving about half of the stent uncovered by the cuff. With this configuration, less cuff material is required compared to a cuff that covers more or all of the stent 200. Less cuff material may allow for the prosthetic heart valve 206 to crimp down to a smaller profile when collapsed. It is contemplated that the cuff may cover any amount of surface area of the cylinder formed by the stent. For example, the upper edge of the cuff may extend straight around the circumference of any cross section of the cylinder formed by the stent. Cuff 260 may be formed of any suitable material, including a biological material such as animal pericardium, or a synthetic material such as UHMWPE.

Figure 8:
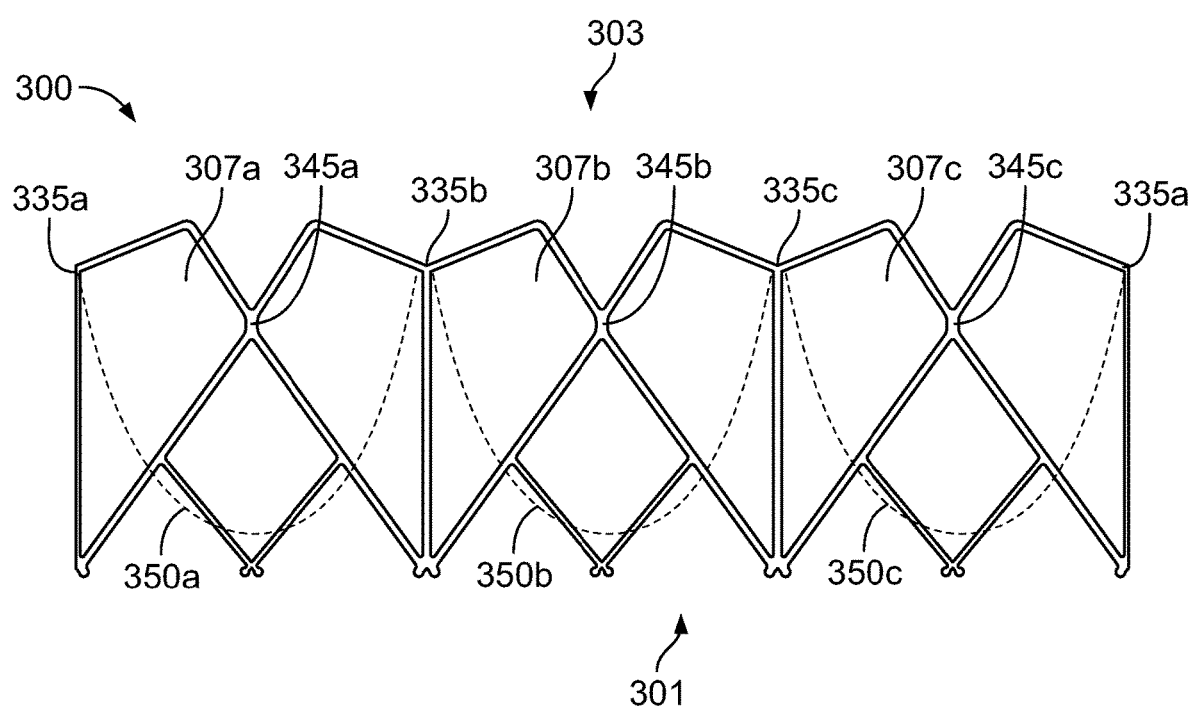
FIG. 8 is a flattened view of a stent according to an alternate embodiment of a prosthetic heart valve.

FIG. 8 illustrates a flattened view of a stent 300 according to an alternate embodiment of the disclosure, as if the stent has been cut longitudinally and laid flat on a table. Unless otherwise stated, like reference numerals refer to like elements of above-described stent 200 but within the 300-series of numbers. Stent 300 has a modified configuration of leaflet attachment, including first leaflet 350a, second leaflet 350b and third leaflet 350c. As with FIG. 6 and leaflets 250a-c, FIG. 8 only illustrates the connection of leaflets 350a-c to the stent 300, and leaflets 350a-c would typically include a free edge, an attached edge, and tabs between the free edges and attachment edges. The attached edge of first leaflet 350a extends from first outer node 335a to second outer node 335b. The attached edge of second leaflet 350b extends from second outer node 335b to third outer node 335c. The attached edge of third leaflet 350c extends from third outer node 335c to first outer node 335a. As described above, each stent section 307a, 307b, 307c has an arcuate shape such that it extends about 120 degrees around the circumference of stent 300. Thus, although FIG. 8 shows a flattened view of stent 300, when assembled as intended, stent 300 will wrap around 360 degrees to form a cylinder such that first leaflet 350a and third leaflet 350c meet at first outer node 335a. Each outer node includes a first end of one leaflet and a second end of another leaflet connected thereto (for example, by sutures). Although leaflets 350 are sutured to outer nodes 335a, 335b, 335c which are positioned nearer outflow end 303 than upper nodes 345a, 345b, 345c, the attached edges of leaflets 350 extend to generally the same axial location near inflow end 301 of stent 300 as leaflets 250 of stent 200 shown in FIG. 6. Thus, larger leaflets (or differently shaped leaflets) may be sutured to stent 300. As with stent 200, stent 300 could alternately include commissure attachment features specifically designed to facilitate attachment of the leaflets to the stent. Leaflets 350 may be formed of any suitable material, including those described in connection with leaflets 250.

Figure 9A:
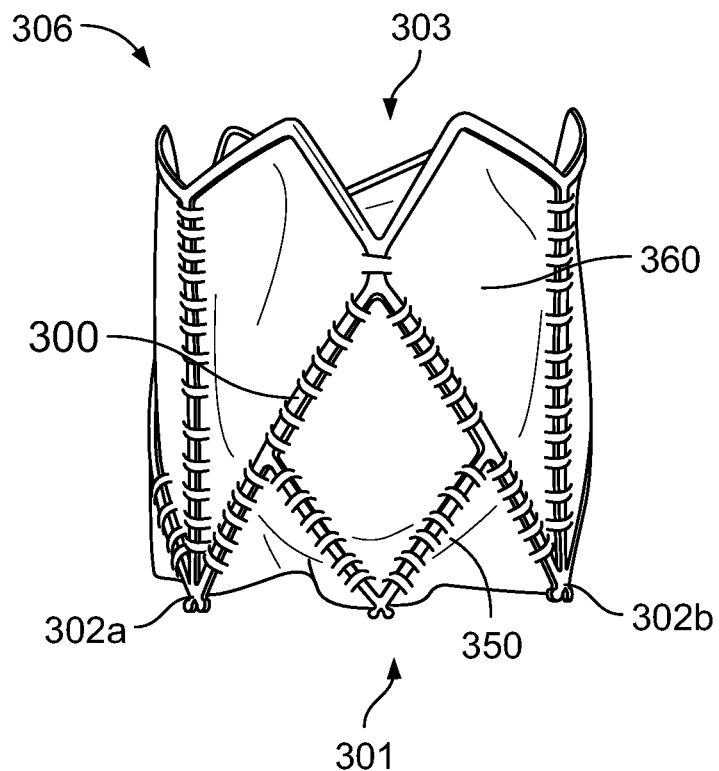
FIGS. 9A-B are front and side views, respectively, of a prosthetic heart valve including the stent of FIG. 8.
Figure 9B:
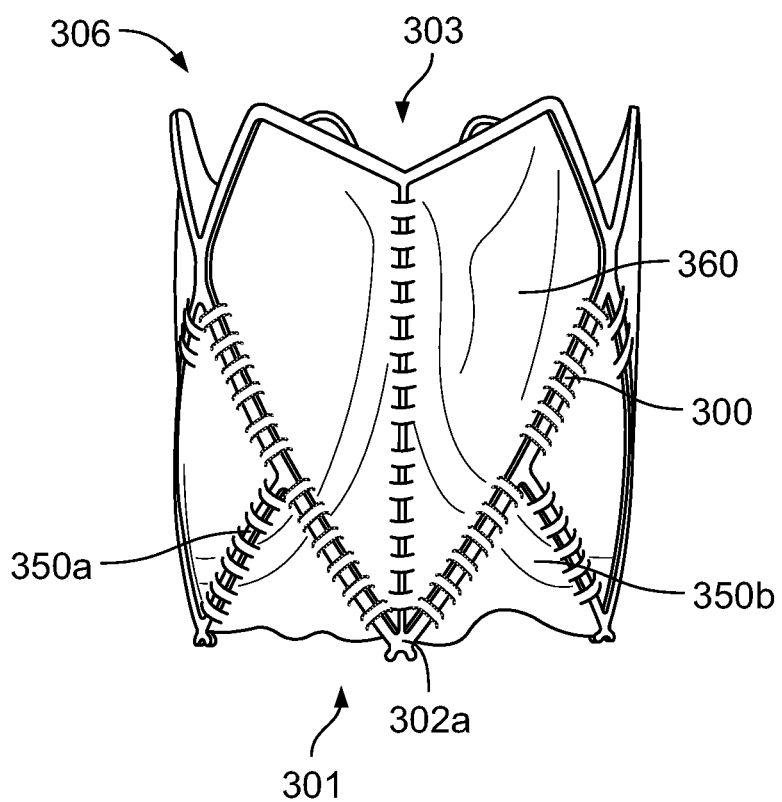

FIGS. 9A-B illustrate valve 306 including stent 300 with cuff 360 coupled (for example with sutures) to stent 300 and leaflets 350a, 350b, 350c coupled (for example with sutures) to cuff 360. Cuff 360 generally covers the entire surface area of the cylinder formed by stent 300. Upper (or outflow) edge of cuff 360 is coupled (for example by sutures) to contour the struts of stent 300 extending along the perimeter of outflow end 303. Lower (or inflow) edge of cuff 360 extends around inflow end 301 between inflow nodes 302a, 302b. As described above, different methods of suturing leaflets 350 to cuff 360 and cuff 360 to stent 300 may be used, many of which are described in U.S. Pat. No. 9,326,856. Cuff 360 may be formed of any suitable material, including those described in connection with cuff 260.

The stent may be formed from biocompatible materials, including metals and metal alloys such as cobalt chrome (or cobalt chromium) or stainless steel, although in some embodiments the stent may be formed of a shape memory material such as nitinol or the like. The stent is thus configured to collapse upon being crimped to a smaller diameter and/or expand upon being forced open, for example via a balloon within the stent expanding, and the stent will substantially maintain the shape to which it is modified when at rest. The stent may be crimped to collapse in a radial direction and lengthen (to some degree) in the axial direction, reducing its profile at any given cross-section, particularly where lengthening has occurred. The stent may also be expanded in the radial direction and foreshortened (to some degree) in the axial direction. Means for modifying the shape of the stent are discussed below in further detail.

Figure 10A:
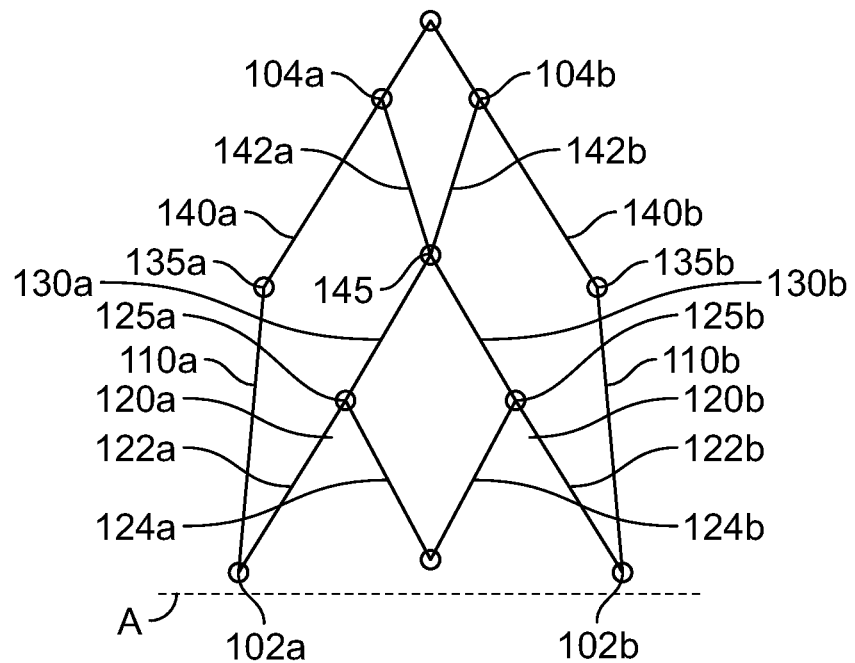
FIGS. 10A-B are schematic views of a portion of the stent section of FIG. 2 in a collapsed state and an expanded state, respectively, relative to axis A.
Figure 10B:
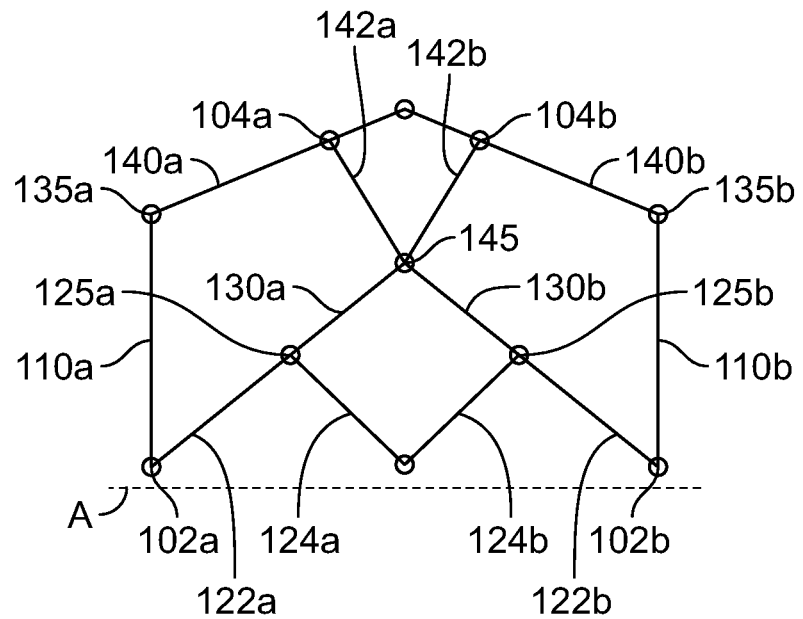

The prosthetic heart valve may be delivered via any suitable transvascular route, for example including transapically or transfemorally. Generally, transapical delivery utilizes a relatively stiff catheter that pierces the apex of the left ventricle through the chest of the patient, inflicting a relatively higher degree of trauma compared to transfemoral delivery. In a transfemoral delivery, a delivery device housing the valve is inserted through the femoral artery and threaded against the flow of blood to the left ventricle. In either method of delivery, the valve may first be collapsed over an expandable balloon while the expandable balloon is deflated. The balloon may be coupled to or disposed within a delivery system, which may transport the valve through the body and heart to reach the aortic valve, with the valve being disposed between the balloon and an overlying sheath. Upon arrival at or adjacent the aortic valve, a surgeon or operator of the delivery system may align the prosthetic valve as desired within the native valve annulus while the prosthetic valve is collapsed over the balloon. When the desired alignment is achieved, the overlying sheath may be withdrawn (or advanced) to uncover the prosthetic valve, and the balloon may then be expanded causing the prosthetic valve to expand in the radial direction, with at least a portion of the prosthetic valve foreshortening in the axial direction. FIGS. 10A-B illustrate how the above-described structure of the stent allows the inflow nodes to remain substantially constant in an axial direction relative the native valve annulus while allowing axial movement of the nodes and struts on the outflow end relative to the native valve annulus.

FIG. 10A depicts a portion of stent 100 in a collapsed state, although it should be understood that the stent of FIG. 10A is illustrated in a flat condition for purposes of illustration whereas, in use, the portion of the stent would be arcuate, forming a part of a cylinder. Although not shown in FIG. 10A, stent 100 may be collapsed over the expandable balloon. Axis A represents the axial location within the native valve annulus or on the expandable balloon with which a surgeon may align inflow nodes 102a, 102b. Upon expansion of the balloon, stent 100 may radially expand and axially foreshorten to assume the expanded state as depicted in FIG. 10B (which is also shown in a generally flattened condition for purposes of illustration only). The stent surface area created by the struts is generally greater on the inflow end than the outflow end, which may create greater friction between the stent and the balloon on the inflow end. In addition, the cuff and/or leaflets are typically positioned nearer the inflow end (see e.g. cuff 260 of FIGS. 7A-B), which may provide even more friction with the balloon nearer the inflow end of the prosthetic heart valve compared to the friction between the outflow end of the prosthetic heart valve and the balloon. Because foreshortening will occur upon expansion of the stent 100 based on the illustrated configuration, the added frictional forces on the inflow end may help hold the inflow end in a substantially constant axial position relative to the balloon and the native valve annulus while most or all of the foreshortening occurs via axial translation of the outflow end relative to the balloon and the native valve annulus.

In the expanded state, inflow nodes 102a, 102b remain substantially in the same axial position relative to axis A. Vertical struts 110a, 110b and outer nodes 135a, 135b translate radially but remain approximately in the same axial position. Lower outer struts 122a, 122b are coupled to inflow nodes 102a, 102b, respectively, which causes radial expansion of the stent at lower outer struts 122a, 122b and consequently axial translation of central nodes 125a, 125b toward axis A. Expansion of the stent at central struts 130a, 130b, inner upper struts 142a, 142 and outer upper struts 140a, 140b thus causes further translation of upper node 145 and outflow nodes 104a, 104b toward axis A. Such movement of the stent allows for a surgeon to more accurately deploy the stent by aligning the inflow end in the proper position of the native annulus prior to expanding the balloon. The surgeon is thus able to rely on the inflow end of the stent remaining substantially in place while the balloon expands as axial translation only occurs among the outflow end.

The inflow nodes may axially translate no more than approximately 4 millimeters during foreshortening relative to the balloon and native mitral valve, whereas outflow nodes may axially translate a relatively larger distance. For example, a stent that may foreshorten a total distance of about 4 millimeters upon transitioning from a collapsed state to an expanded state may experience axial translation of the inflow nodes of anywhere between approximately 0 and 4 millimeters. In some examples, the inflow nodes may translate about 0 millimeters while the outflow nodes translate about 4 millimeters. In other examples, both the inflow and outflow nodes may translate about 2 millimeters. In an alternate embodiment, a stent that is configured to foreshorten a total distance of approximately 6 millimeters may experience axial translation at the inflow nodes between 0 and 6 millimeters. As described above, the axial translation of the outflow nodes is generally expected to be greater than the translation of the inflow nodes.

Expanding on the paragraph above, it should be understood that the vertical struts (e.g. vertical struts 110a-c) are nearly aligned with the longitudinal axis of the stent 100 when the stent is collapsed, and are fully or nearly fully aligned with the longitudinal axis of the stent when the stent is expanded. In other words, the stent cannot foreshorten or lengthen to any significant degree at the vertical struts. However, the configuration of the remaining struts (which may generally be referred to as oblique struts), including the various diamond and/or kite-shaped cells, introduce the ability of some amount of lengthening and foreshortening during collapsing and expanding, respectively. However, in a traditional stent that foreshortens upon expansion, the inflow and outflow ends will both move axially relative to the balloon (if the stent is balloon expandable) and the native valve annulus, meaning that the position of the prosthetic leaflets will generally shift axially relative to the native valve annulus during expansion. With stent 100, the inclusion of vertical struts to reduce the total amount of foreshortening, and the configuration of the struts (and/or the cuff and/or leaflets) to include a larger amount of friction with the balloon at the inflow end of the prosthetic heart valve, may result in little or no axial shifting of the inflow end of the prosthetic heart valve relative to the native valve annulus during expansion. But, as described above, some amount of lengthening and foreshortening may be desirable in order to allow the prosthetic heart valve to distribute its overall bulk along a greater length to allow for a smaller overall profile when collapsed. The diamond and kite-shaped cells allow for that desirable lengthening and foreshortening, but the overall configuration of the prosthetic heart valve generally limits that lengthening and foreshortening to occur at the outflow end of the prosthetic heart valve. Stated another way, the prosthetic heart valve(s) described herein provide some or all of the benefits of allowing the prosthetic heart valve to lengthen and foreshorten, while avoiding some or all of the problems of allowing the prosthetic heart valve to lengthen and foreshorten.

Figure 11A:
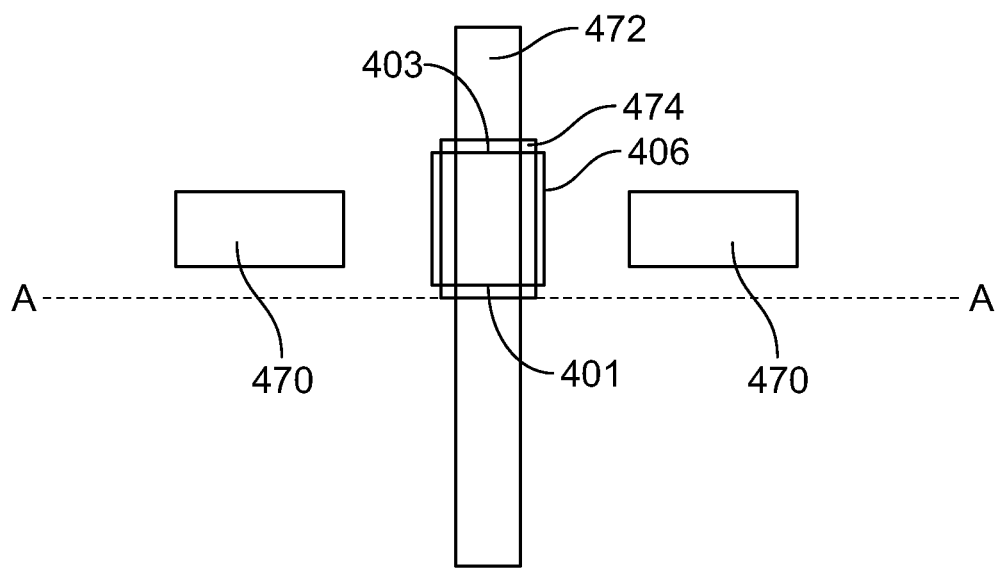
FIGS. 11A-B are schematic representations of a prosthetic heart valve delivered to a native valve annulus via a delivery device, the heart valve in a collapsed and expanded state, respectively.
Figure 11B:
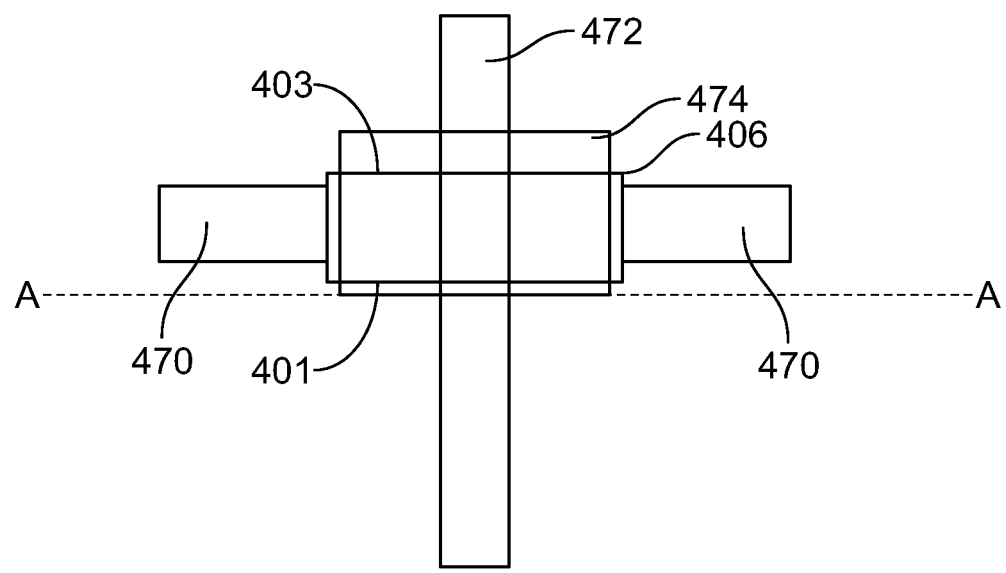

A schematic representation of the expansion of a prosthetic heart valve 406 in a native valve annulus 470 is illustrated in FIGS. 11A-B. As described above, prosthetic heart valve 406 may be disposed over a balloon 474 coupled to a delivery device 472. Delivery device 472 may also include an overlying sheath (not shown) covering prosthetic heart valve 406 during delivery. Prior to delivery, prosthetic heart valve 406 is crimped to a collapsed state over a deflated balloon 474 to decrease profile and promote ease of delivery to native valve annulus 470. FIG. 11A illustrates balloon 474 in a deflated stated and prosthetic heart valve 406 in a collapsed state as delivery device 472, balloon 474 and prosthetic heart valve 406 are delivered to native valve annulus 470. It should be understood that FIGS. 11A-B illustrate a cross-sectional view of native valve annulus 470, which extends 360 degrees around delivery device 472, but only two sides are shown for ease of illustration. A surgeon may align inflow end 401 of prosthetic heart valve 406 with axis A when positioning valve 406 relative to native valve annulus 470. When prosthetic heart valve 406 is positioned as desired, the surgeon may inflate balloon 474, transitioning valve 406 to an expanded state as shown in FIG. 11B. As described above, inflow end 401 of prosthetic heart valve 406 may remain substantially aligned with axis A upon expansion while outflow end 403 may translate relative to balloon 474 due to foreshortening of valve 406. Balloon 474 may inflate to expand prosthetic heart valve 406 such that the outer surface of valve 406 substantially abuts the inner surface of native valve annulus 470. The stent of prosthetic heart valve 406 is preferably composed of a material such that the stent maintains its shape after balloon 474 is inflated and valve 406 has achieved an expanded state. After prosthetic heart valve 406 is expanded, the balloon 474 may be deflated, and delivery device 472 may be retracted. Prosthetic heart valve 406 is preferably placed in an aortic valve, but it is contemplated that it may be delivered in any heart valve.

A machine may be used to crimp the prosthetic heart valve over the balloon prior to delivery. The machine may apply a designated force to crimp the valve over the balloon. The size to which the valve may collapse may be determined by the structure of the valve. A prosthetic heart valve according to an embodiment disclosed herein having a diameter in an expanded condition of about 23 millimeters may require about 11.1 newtons (N) of force to be crimped to a diameter of about 10 millimeters, whereas a prosthetic heart valve having a structure as described in U.S. Pat. No. 8,454,685 having a diameter in an expanded state of about 23 millimeters may require a force of about 27.0 N to be crimped to a diameter of about 10 millimeters. The prosthetic valve disclosed herein having the same expanded diameter as the prior art while requiring less force to be crimped to a particular crimped diameter may thus be capable of being crimped to a smaller size when a greater force is applied. In other words, a typical crimping device may be capable of applying some particular maximum crimping force, such as about 30 N. Thus, the prosthetic heart valve disclosed herein may be configured to collapse to a smaller size than the valve having a structure as disclosed in U.S. Pat. No. 8,454,685 upon application of the same crimping force to each valve. Although delivery devices with balloon expansion and crimping devices are not described in great detail herein, it should be understood that prior art balloon expansion delivery devices and prior art crimping devices may be used with the prosthetic heart valve(s) described herein. For example, U.S. Pat. No. 7,818,861 describes a crimping device which may be suitable for use with the prosthetic heart valve(s) described herein, and that patent is hereby incorporated by reference herein. One exemplary delivery device with an expandable balloon that may be suitable for use with the prosthetic valve(s) described herein is described in U.S. Pat. No. 10,179,047, the disclosure of which is hereby incorporated by reference herein.

According to one aspect of the disclosure, a prosthetic heart valve comprises:

a collapsible and expandable stent extending in an axial direction from a first inflow end to a second outflow end, the collapsible and expandable stent having a plurality of vertical struts that are parallel to the axial direction in an expanded condition of the stent, and a plurality of oblique struts that are oblique to the axial direction in the expanded condition of the stent;

a cuff coupled to the stent; and a plurality of prosthetic leaflets disposed within the stent, the plurality of prosthetic leaflets configured to allow blood to flow in an antegrade direction from the first inflow end toward the second outflow end of the stent, and to substantially block blood from flowing in a retrograde direction from the second outflow end of the stent toward the first inflow end of the stent, wherein the plurality of oblique struts are coupled to the plurality of vertical struts so that, upon transitioning from the collapsed condition to the expanded condition, the first inflow end of the stent remains substantially static relative to the axial direction while the second outflow end of the stent moves in the axial direction toward the first inflow end; and/or the plurality of vertical struts includes three vertical struts, and the plurality of prosthetic leaflets includes three prosthetic leaflets; and/or the stent includes three sections of the plurality of oblique struts, each section being positioned circumferentially between an adjacent pair of vertical struts, and each section being symmetric and having an arcuate shape extending about 120 degrees around a circumference of the stent; and/or each section of the plurality of oblique struts includes a first pair of oblique struts forming a first half-diamond shaped cell at the first inflow end of the stent, and a second pair of oblique struts forming a second half-diamond shaped cell at the first inflow end of the stent; and/or the first pair of oblique struts includes a first oblique strut coupled to the first end of a first one of the vertical struts, and a second oblique strut, and the second pair of oblique struts includes a third oblique strut coupled to the second oblique strut at the first inflow end of the stent, and a fourth oblique strut coupled to the first end of a second one of the vertical struts; and/or each section of the plurality of oblique struts includes fifth and sixth oblique struts coupled to each other, the fifth oblique strut coupled to the second oblique strut, and the sixth oblique strut coupled to the third oblique strut, so that together the second, third, fifth, and sixth oblique struts form a diamond-shaped cell, the diamond-shaped cell being positioned substantially midway between the first and second ones of the vertical struts; and/or each section of the plurality of oblique struts includes a seventh oblique strut coupled to the second end of the first one of the vertical struts, and an eighth oblique strut coupled to the second end of the second one of the vertical struts, the seventh and eighth oblique struts each extending from the respective ones of the vertical struts toward the second outflow end of the stent where the seventh and eighth oblique struts connect to each other; and/or each section of the plurality of oblique struts includes a ninth oblique strut coupling the seventh oblique strut to the diamond-shaped cell, and a tenth oblique strut coupling the eighth oblique strut to the diamond-shaped cell; and/or the ninth oblique strut, the tenth oblique strut, and portions of the seventh and eighth oblique struts together form a kite-shaped cell, the kite-shaped cell being aligned with the diamond-shaped cell in the axial direction; and/or each section of the plurality of oblique struts includes a seventh oblique strut coupled to the second end of the first one of the vertical struts, and an eighth oblique strut coupled to the second end of the second one of the vertical struts, the seventh and eighth oblique struts each extending from the respective ones of the vertical struts toward the second outflow end of the stent; and/or each section of the plurality of oblique struts includes a ninth oblique strut coupling an end of the seventh oblique strut to the diamond-shaped cell, and a tenth oblique strut coupling an end of the eighth oblique strut to the diamond-shaped cell; and/or the ninth oblique strut and the tenth oblique strut together form a third half-diamond shaped cell, the third half-diamond shaped cell being axially aligned with the diamond-shaped cell; and/or each of the plurality of leaflets includes a free edge adapted to move radially toward and away from the stent, and an attached edge coupled to the stent; and/or each attached edge of each of the plurality of leaflets extends from a first attachment point at a first node between the fifth, sixth, ninth, and tenth oblique struts of a first section of the plurality of oblique struts to a second attachment point at a second node between the fifth, sixth, ninth, and tenth oblique struts of a second section of the plurality of oblique struts; and/or the cuff includes an inflow end substantially aligned with the first inflow end of the stent, and the cuff includes an outflow end that is positioned between the first inflow end of the stent and the second outflow end of the stent.

According to another embodiment of the disclosure, a method of implanting a prosthetic heart valve comprises:

positioning the prosthetic heart valve in a collapsed condition over an expandable balloon attached to a delivery system such that the prosthetic heart valve surrounds the expandable balloon, wherein the prosthetic heart valve has a first inflow end disposed at a first axial position on the expandable balloon and a second outflow end disposed at a second axial position on the expandable balloon;

inserting the delivery system through a patient until the prosthetic heart valve is adjacent the native valve annulus;

aligning the first inflow end of the prosthetic heart valve with a desired axial location in the native valve annulus while the prosthetic heart valve is in the collapsed condition; and expanding the balloon to transition the prosthetic heart valve into an expanded condition such that the prosthetic heart valve radially expands and axially foreshortens, wherein, during radial expansion, the first inflow end of the prosthetic heart valve axially translates no more than 4 millimeters from the first axial position; and/or during radial expansion of the prosthetic heart valve, the second outflow end of the prosthetic heart valve axially translates along the expandable balloon toward the first axial position; and/or positioning the prosthetic heart valve in the collapsed condition includes crimping the prosthetic heart valve over the balloon from the expanded condition to the collapsed condition; and/or the prosthetic heart valve axially lengthens during crimping; and/or expanding the balloon causes the second outflow end to translate an axial distance greater than the first inflow end; and/or the crimping step includes crimping the prosthetic heart valve from a diameter of about 23 millimeters in the expanded condition to a diameter of about 10 millimeters in the collapsed condition by applying a crimping force of between about 10N and about 12N.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
a collapsible and expandable stent extending in an axial direction from a first inflow end to a second outflow end, the collapsible and expandable stent having a plurality of vertical struts that are parallel to the axial direction in an expanded condition of the stent, and a plurality of oblique struts that are oblique to the axial direction in the expanded condition of the stent;
a cuff coupled to the stent; and
a plurality of prosthetic leaflets disposed within the stent, the plurality of prosthetic leaflets configured to allow blood to flow in an antegrade direction from the first inflow end toward the second outflow end of the stent, and to substantially block blood from flowing in a retrograde direction from the second outflow end of the stent toward the first inflow end of the stent,
wherein the plurality of oblique struts are coupled to the plurality of vertical struts so that, upon transitioning from the collapsed condition to the expanded condition, the first inflow end of the stent remains substantially static relative to the axial direction while the second outflow end of the stent moves in the axial direction toward the first inflow end; wherein each section of the plurality of oblique struts includes a first pair of oblique struts forming a first half-diamond shaped cell at the first inflow end of the stent, and a second pair of oblique struts forming a second half-diamond shaped cell at the first inflow end of the stent; the first pair of oblique struts includes a first oblique strut coupled to the first end of a first one of the vertical struts, and a second oblique strut, and the second pair of oblique struts includes a third oblique strut coupled to the second oblique strut at the first inflow end of the stent, and a fourth oblique strut coupled to a first end of a second one of the vertical struts; and wherein each section of the plurality of oblique struts includes fifth and sixth oblique struts coupled to each other, the fifth oblique strut coupled to the second oblique strut, and the sixth oblique strut coupled to the third oblique strut, so that together the second, third, fifth, and sixth oblique struts form a diamond-shaped cell, the diamond-shaped cell being positioned substantially midway between first and second ones of the vertical struts.

2. The prosthetic heart valve of claim 1, wherein the plurality of vertical struts includes three vertical struts, and the plurality of prosthetic leaflets includes three prosthetic leaflets.

3. The prosthetic heart valve of claim 2, wherein the stent includes three sections of the plurality of oblique struts, each section being positioned circumferentially between an adjacent pair of vertical struts, and each section being symmetric and having an arcuate shape extending about 120 degrees around a circumference of the stent.

4. The prosthetic heart valve of claim 3, wherein each section of the plurality of oblique struts includes a seventh oblique strut coupled to the second end of the first one of the vertical struts, and an eighth oblique strut coupled to the second end of the second one of the vertical struts, the seventh and eighth oblique struts each extending from the respective ones of the vertical struts toward the second outflow end of the stent where the seventh and eighth oblique struts connect to each other.

5. The prosthetic heart valve of claim 4, wherein each section of the plurality of oblique struts includes a ninth oblique strut coupling the seventh oblique strut to the diamond-shaped cell, and a tenth oblique strut coupling the eighth oblique strut to the diamond-shaped cell.

6. The prosthetic heart valve of claim 5, wherein the ninth oblique strut, the tenth oblique strut, and portions of the seventh and eighth oblique struts together form a kite-shaped cell, the kite-shaped cell being aligned with the diamond-shaped cell in the axial direction.

7. The prosthetic heart valve of claim 3, wherein each section of the plurality of oblique struts includes a seventh oblique strut coupled to the second end of the first one of the vertical struts, and an eighth oblique strut coupled to the second end of the second one of the vertical struts, the seventh and eighth oblique struts each extending from the respective ones of the vertical struts toward the second outflow end of the stent.

8. The prosthetic heart valve of claim 7, wherein each section of the plurality of oblique struts includes a ninth oblique strut coupling an end of the seventh oblique strut to the diamond-shaped cell, and a tenth oblique strut coupling an end of the eighth oblique strut to the diamond-shaped cell.

9. The prosthetic heart valve of claim 8, wherein the ninth oblique strut and the tenth oblique strut together form a third half-diamond shaped cell, the third half-diamond shaped cell being axially aligned with the diamond-shaped cell.

10. The prosthetic heart valve of claim 9, wherein each of the plurality of leaflets includes a free edge adapted to move radially toward and away from the stent, and an attached edge coupled to the stent.

11. The prosthetic heart valve of claim 10, wherein each attached edge of each of the plurality of leaflets extends from a first attachment point at a first node between the fifth, sixth, ninth, and tenth oblique struts of a first section of the plurality of oblique struts to a second attachment point at a second node between the fifth, sixth, ninth, and tenth oblique struts of a second section of the plurality of oblique struts.

12. The prosthetic heart valve of claim 11, wherein the cuff includes an inflow end substantially aligned with the first inflow end of the stent, and the cuff includes an outflow end that is positioned between the first inflow end of the stent and the second outflow end of the stent.

* * * * *